United States Patent [19]

Shimizu et al.

[11] Patent Number: 5,081,279
[45] Date of Patent: Jan. 14, 1992

[54] PRODUCTION OF α-(3-BENZOYLPHENYL)PROPIONIC ACID DERIVATIVE

[75] Inventors: Isoo Shimizu; Yasuo Matsumura, both of Yokohama; Yoshihisa Inomata, Kawasaki, all of Japan

[73] Assignee: Nippon Petrochemicals Company, Limited, Tokyo, Japan

[21] Appl. No.: 602,240

[22] PCT Filed: Mar. 6, 1990

[86] PCT No.: PCT/JP90/00288
§ 371 Date: Nov. 6, 1990
§ 102(e) Date: Nov. 6, 1990

[87] PCT Pub. No.: WO90/10614
PCT Pub. Date: Sep. 20, 1990

[30] Foreign Application Priority Data

Mar. 6, 1989 [JP] Japan .................................. 1-53479

[51] Int. Cl.$^5$ .............................................. C07C 69/76
[52] U.S. Cl. ........................................ 560/52; 562/460; 562/406
[58] Field of Search ............... 560/52; 562/406, 460

[56] References Cited

U.S. PATENT DOCUMENTS

| | | | |
|---|---|---|---|
| 4,035,376 | 7/1977 | Janssen et al. | 562/460 |
| 4,097,522 | 6/1978 | Baiocchi | 562/460 |
| 4,230,884 | 10/1980 | Zupancic | 562/460 |
| 4,329,507 | 5/1982 | Takeda et al. | 560/52 |
| 4,350,825 | 9/1982 | Huang | 562/406 |
| 4,789,756 | 12/1988 | Drenk | 562/406 |
| 4,889,952 | 12/1989 | Shimizu | 560/52 |
| 4,910,337 | 3/1990 | Chiu | 562/460 |

FOREIGN PATENT DOCUMENTS

| | | |
|---|---|---|
| 170147 | 2/1986 | European Pat. Off. |
| 284310 | 9/1988 | European Pat. Off. |
| 1668645 | 7/1973 | Fed. Rep. of Germany |

*Primary Examiner*—Paul J. Killos
*Attorney, Agent, or Firm*—Scully, Scott, Murphy & Presser

[57] ABSTRACT

This invention provides a method of producing highly pure α-(3-benzoylphenyl)propionic acid derivatives, which are medicines per sec or which can easily afford the same, from readily available 3-ethylbenzophenone in a very simplified manner efficiently and economically. The method comprises dehydrogenating 3-ethylbenzophenone in vapor phase in the presence of an inert gas and carbonylating the formed 3-ethenylbenzophenone in the presence of a carbonylation catalyst comprising a transition metal complex.

4 Claims, No Drawings

PRODUCTION OF α-(3-BENZOYLPHENYL)PROPIONIC ACID DERIVATIVE

DESCRIPTION

1. Technical Field

This invention relates to a method of producing α-(3-benzoylphenyl)propionic acid derivatives. More particularly, the invention relates to an efficient and economical method of producing highly pure α-(3-benzoylphenyl)propionic acid derivatives.

Incidentally, the α-(3-benzoylphenyl)propionic acid is excellent in the relief of fever, pain and inflammation and it is a useful substance which is known by a trade name of Ketoprofen.

2. Background Art

In the class of substituted arylpropionic acids, there are many compounds which can be used intact as medicines and various kinds of preparation methods have been hitherto proposed. Among them, α-(3-benzoylphenyl)propionic acid is excellent in the relief of fever, pain and inflammation and it is a useful substance as a trade name of Ketoprofen.

The α-(3-benzoylphenyl)propionic acid derivatives as the subject materials in the present invention are represented by the following general formula (C). In the formula, when X is a hydroxyl group, the formula represents Ketoprofen. When X is hydrogen or X is an alkoxyl group, the compound is easily converted into Ketoprofen by being oxidized or by being hydrolyzed through ordinary methods, respectively.

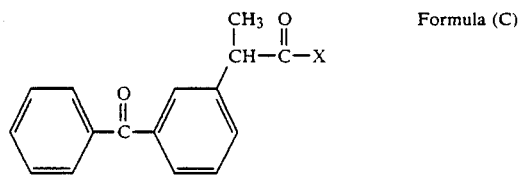

Formula (C)

wherein X is hydrogen, a hydroxyl group or an alkoxyl group.

With regard to the preparation of Ketoprofen, several kinds of methods have been proposed. The following methods are typical ones.

(1) 3-Benzoylpropiophenone is reacted with methyl orthoformate in the presence of thallium nitrate to obtain methyl ester of Ketoprofen. This is hydrolyzed by a conventional method to obtain Ketoprofen (British Patent No. 2,019,393).

(2) 3-Acetylbenzophenone and chloroform are reacted in a basic condition in the presence of a quaternary ammonium salt to obtain α-arylpropenoic acid, which is then subjected to catalytic reductive hydrogenation with a catalyst of palladium-carbon to obtain Ketoprofen (Japanese Laid-Open Patent Publication No. 55-7225).

Both the above methods are, however, not satisfactory as industrial production methods because toxic thallium is used, the preparation of starting materials themselves is difficult, and the processes are not efficient due to their low yields.

In addition, with regard to the dehydrogenation of benzophenone, it is known that, in the presence of a hydrogen donor, the carbonyl group of benzophenone is easily hydrocracked in the reaction system by the hydrogen which is generated from the hydrogen donor and it is converted into diphenylmethane (Fuel, Vol. 57, p. 650 (1978)). In other words, the carbonyl group connected between the adjacent two phenyl groups is highly activated, and as a result, the carbonyl group is liable to suffer hydrocracking, which is different from methyl ethyl ketone or else. Accordingly, it is supposed that, when ethylbenzophenone is dehydrogenated, a compound having a diphenylmethane structure, rather than ethenylbenzophenone, is produced.

According to the results of investigation carried out by the present inventors with regard to the catalytic dehydrogenation of ethylbenzophenone, however, the initially expected compound having diphenylmethane structure is hardly produced by a specific method, and to their surprise, it was found out that ethenylbenzophenone is produced in a high yield.

Accordingly, the object of the present invention is to produce efficiently highly pure α-(3-benzoylphenyl)propionic acid derivatives by dehydrogenating 3-ethylbenzophenone and then carbonylating.

DISCLOSURE OF INVENTION

The present invention provides a method for producing α-(3-benzoylphenyl)propionic acid derivative characterized in the following step (I) and step (II).

Step (I)

A step of vapor phase dehydrogenation by bringing 3-ethylbenzophenone represented by a formula (A) into contact with a dehydrogenation catalyst in the coexistence of an inert gas through a fixed bed flow method to obtain 3-ethenylbenzophenone represented by a formula (B), and

Step (II)

A step to obtain α-(3-benzoylphenyl)propionic acid derivative represented by a general formula (C) in which 3-ethenylbenzophenone represented by the formula (B) obtained in the step (I) is subjected to carbonylation with carbon monoxide and hydrogen or with carbon monoxide and water or a lower alcohol having 1 to 4 carbon atoms at a temperature of 40° C. to 200° C. and a reaction pressure of 5 kg/cm² or above in the presence of a transition metal complex carbonylation catalyst.

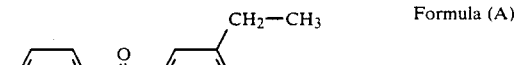

Formula (A)

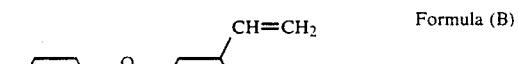

Formula (B)

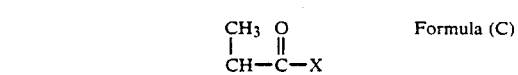

Formula (C)

wherein X is hydrogen, a hydroxyl group or an alkoxyl group.

The starting material in the method of the present invention is 3-ethylbenzophenone represented by the formula (A).

The 3-ethylbenzophenone can be produced by conventionally known methods and those prepared by any method can be used without difficulty. Exemplified as typical methods are: a method to react benzophenone with an ethylation reagent such as diethyl sulfate in the presence of a Friedel-Crafts catalyst such as anhydrous aluminum chloride; a method to oxidize 3-ethyldiphenylmethane with a strong oxidizing agent such as permanganate or with molecular oxygen; a method to oxidize 3-ethyldiphenylethylene with a strong oxidizing agent such as permanganate or with molecular oxygen; and a method to react 3-ethyldiphenylethane with hot diluted nitric acid.

According to the investigation carried out by the present inventors, for example, metal oxide catalysts such as those hitherto used for the dehydrogenation of ethylbenzene to obtain styrene, can be used as the dehydrogenation catalyst in the step (I) of the present invention. Exemplified as such catalysts are iron oxide catalyst, chromium oxide catalyst and a mixture of these oxides. These catalysts may contain the main components of iron oxide, chromium oxide or their mixture and a suitable quantity of oxides of magnesium, molybdenum, vanadium, manganese, zinc, copper and the like as a promoter. Furthermore, in order to improve the dehydrogenation efficiency, the oxides of alkali metals such as sodium and potassium and alkaline earth metals such as calcium and barium can be added. The catalyst can be composed of the main component of iron oxide or chromium oxide itself, or it may be a carrier-supported catalyst on a suitable carrier of alumina, silica-alumina or silica. Because the metal oxide catalyst is generally in solid state, it can be used in a fixed bed.

The step (I) of the present invention is carried out in a diluted condition in the presence of an inert gas. This inert gas can be arbitrarily selected from those which do not hinder the reaction of dehydrogenation and do not act as catalyst poison for the dehydrogenation catalyst. Exemplified as such inert gases are inorganic gases such as nitrogen, hydrogen, helium, argon, and steam and organic gases such as methane. Among these inert gases, steam is a preferable diluent in view of practical handling.

In the dilution with an inert gas, the molar ratio of the inert gas to 3-ethylbenzophenone to an inert gas is preferably 10 or higher. When the ratio of dilution is too low, it is not desirable in that the dehydrogenation efficiency is low and the reaction is not effectual, at the same time, the life of catalyst is shortened due to coking. The more the ratio of the inert gas, the higher the efficiency. In practice, however, the upper limit of the molar ratio to 3-ethylbenzophenone is about 500.

In order to improve the rate of reaction in dehydrogenation, the coexistence of oxygen as a hydrogen acceptor can be allowed.

The temperature of contact with the dehydrogenation catalyst is in the range of 400° C. to 650° C., preferably 500° C. to 600° C. The temperatures lower than 400° C. are not desirable in practice because the dehydrogenation efficiency is low. On the other hand, the temperatures above 650° C. is not desirable either, because the catalytic cracking and hydrocracking by the produced hydrogen, of 3-ethylbenzophenone itself becomes intense.

In view of the equilibrium of dehydrogenation reaction, the pressure in the dehydrogenation is preferably low, however, it is generally in the range of reduced pressure to 10 kg/cm$^2$, preferably from reduced pressure to 5 kg/cm$^2$.

The 3-ethylbenzophenone is substantially dehydrogenated in vapor phase. When occasion demands, a part of it can be in liquid phase, however, it is desirable that 3-ethylbenzophenone is completely in vapor phase.

With regard to the factor relative to the reaction time, the LHSV is selected from the range of 0.001 to 100 hr$^{-1}$, preferably 0.01 to 10 hr$^{-1}$. When the LHSV value is lower than the above range, the yield is lowered due to the hydrocracking and polymerization of reaction product. Furthermore, in the case that the LHSV value is larger than the above range, it is not desirable because the dehydrogenation efficiency and also the yield are lowered.

It is to be noted that, in the method of the present invention, the vapor phase dehydrogenation must be carried out in a fixed bed flow reaction system. The reason for this is that, as described in the foregoing paragraphs, because the carbonyl group of benzophenone is easily hydrocracked by liberated hydrogen, the retention time in the reaction system must be as short as possible. In the present invention, also in view of the prevention of the polymerization of the produced 3-ethenylbenzophenone, the vapor phase dehydrogenation in a fixed bed is important. Accordingly, the liquid phase dehydrogenation and batchwise reaction are not desirable because their yields are not high.

It is more preferable as dehydrogenation conditions that the particle diameter of a dehydrogenation catalyst is 25% or less relative to the inner diameter of reaction tubes of a fixed bed reactor and the starting material of 3-ethylbenzophenone is passed through the catalyst bed at a linear velocity (on the basis of empty column, vapor phase, hereinafter referred to as "LV") of 50 m/hr or higher.

It is known that, when the diameter of catalyst is large as compared with the diameter of reaction tube, the inside wall of the reaction tube has an influence on the reaction. Furthermore, when the LV value exceeds a certain level, it has also an influence on the reaction. However, it cannot be anticipated at all that these influences are given markedly on a specific reaction like in the method of the present invention.

After the reaction, in order to avoid the side reaction such as the polymerization of ethenyl group, the reaction mixture must be cooled and liquefied without delay. In addition, when steam is used as a heating medium, the separation from water is necessary.

In the step (I) of the present invention, 3-ethylbenzophenone is dehydrogenated under the above-described conditions to obtain 3-ethenylbenzophenone of the formula (B).

Partially unchanged 3-ethylbenzophenone as the starting material is contained in the effluent, which depends upon the dehydrogenation efficiency. Such an effluent can be fed to the next step (II) without any difficulty.

The dehydrogenation product from the foregoing step (I) is then subjected to a conventional separation method such as distillation to recover a fraction containing 3-ethenylbenzophenone and passed to the next step.

The boiling point of 3-ethenylbenzophenone obtained in this step (I) and that of 3-ethylbenzophenone as a starting material are so close to each other that the separation of them by means of an industrial separation method such as conventional distillation is difficult. Furthermore, the separation by precise fractional distillation is also not desirable because the loss due to the polymerization of 3-ethenylbenzophenone is caused to occur. Therefore, as far as the separation is done by an industrial method, the fraction to be fed to the next step cannot help containing at least 3-ethylbenzophenone and 3-ethenylbenzophenone together. However, when the material is passed from the step (I) to the step (II), it is not necessary to separate the reaction product obtained in the step (I). Furthermore, as described above, the separation of 3-ethenylbenzophenone of the formula (B) and the starting material, 3-ethylbenzophenone of the formula (A) is difficult in practice. As described, it is not necessary to refine the reaction product obtained in dehydrogenation step (I), however, the side reaction products in the step (I) such as lighter decomposition products and heavier polymerization products can be separated when occasion demands.

Accordingly, the present invention is characterized in that the reaction product of the step (I) is recovered by simple operation of industrial distillation and then it can be fed to the step (II).

The fraction which is fed to the step (II) as a reaction material is the one which is obtained from the step (I) by distillation and contains main components of 80° to 170° C., preferably 90° to 160° C. in boiling range at 1 to 3 mm Hg in vacuum.

In the step (II) of the present invention, the reaction product containing 3-ethenylbenzophenone obtained in the step (I) is carbonylated with carbon monoxide and hydrogen or with carbon monoxide and water or lower alcohol having 1 to 4 carbon atoms to obtain α-(3-benzoylphenyl)propionic acid derivative. The positions of substituent groups in the reaction material are maintained intact in the carbonylation product.

The alcohols are those having 1 to 4 carbon atoms which are exemplified by methanol, ethanol, propanol, isopropanol and butanol. Alcohols having 5 or more carbon atoms are not desirable because the reaction rate of carbonylation is low.

The transition metal carbonylation catalysts used in the present invention are those containing active metals of Pd, Pt, Rh, Ir, Ru, Co and Ni. As the active metals, those having oxidation numbers from 0 to the highest numbers can be used. Usable complexes are those having ligands of halogen atoms, trivalent phosphorus compounds, π-allyl group, amines, nitriles, oximes, olefins, hydrogen, or carbon monoxide.

The transition metal carbonylation complex catalysts are exemplified by bistriphenylphosphine dichlorocomplex, bistributylphosphine dichlorocomplex, bistricyclohexylphosphine dichlorocomplex, π-allyltriphenylphosphine dichlorocomplex, triphenylphosphine piperidine dichlorocomplex, bisbenzonitrile dichlorocomplex, biscyclohexyloxime dichlorocomplex, 1,5,9-cyclododecatriene dichlorocomplex, bistriphenylphosphine dicarbonyl complex, bistriphenylphosphine acetate complex, bistriphenylphosphine dinitrate complex, bistriphenylphosphine sulfate complex, tetrakistriphenylphosphine complex; and complexes in which a part of ligands are carbon monoxide such as chlorocarbonyl bistriphenylphosphine complex, hydridocarbonyl triphenylphosphine complex, bischlorotetracarbonyl complex and dicarbonyl acetylacetonate complex.

Furthermore, the compounds which can produce the above metal complexes in the reaction system can be also used by being fed to the reaction system. That is, phosphine, nitrile, allyl compound, amine, oxime, olefin or carbon monoxide which is able to be the ligands to the oxides, sulfates, chlorides or acetates of the above transition metals, can be simultaneously added into the reaction system.

The above phosphines are exemplified by triphenylphosphine, tritolylphosphine, tributylphosphine, tircyclohexylphosphine and triethylphosphine. The nitriles are exemplified by benzonitrile, acrylonitrile, propionitrile and benzylnitrile. The allyl compounds are exemplified by allyl chloride and allyl alcohol. The amines are exemplified by benzylamine, pyridine, piperazine and tri-n-butylamine. The oximes are exemplified by cyclohexyloxime, acetoxime and benzaldoxime. The olefins are exemplified by 1,5-cyclooctadiene and 1,5,9-cyclodecatriene.

Furthermore, in order to improve the reaction rate, inorganic halides such as hydrogen chloride and boron trifluoride and organic iodide such as methyl iodide can be added.

When these halides are added, 0.1 to 30 moles, preferably 1 to 15 moles as halogen atom are used relative to 1 mole of the transition metal carbonylation catalyst or active metal compound. When the addition quantity is less than 0.1 mole, the effect of addition is not obtained sometimes, which depends upon the kind of catalyst. When the addition quantity exceeds 30 times by mole, it is not desirable in that the catalytic activity is rather lowered, and at the same time, a side reaction, other than the aimed reaction, to add halogen to the double bonds of 3-ethenylbenzophenone as a starting material is caused to occur.

The use quantity of transition metal carbonylation catalyst or active metal compound which can produce transition metal carbonylation catalyst is 0.0001 to 0.5 mole, preferably 0.001 to 0.1 mole to one mole of 3-ethenylbenzophenone of the formula (B). When the active metal compound is used, the addition quantity of the compound to form ligands is 0.8 to 10 moles, preferably 1 to 4 moles, to one mole of the active metal compound.

The carbonylation is continued until the lowering of pressure owing to the absorption of carbon monoxide is not observed when the reaction is done in the coexistence of water or alcohol having 1 to 4 carbon atoms and the reaction is continued until the lowering of pressure owing to the absorption of the mixed gas of carbon monoxide and hydrogen is not observed when the reaction is done in the coexistence of hydrogen. The reaction time of 4 to 20 hours is generally sufficient.

When carbon monoxide and hydrogen are used together, the carbon monoxide and hydrogen for the reaction can be fed either separately or by mixing them previously. The molar ratio of carbon monoxide and hydrogen to be fed into reaction system can be selected arbitrarily. More particularly, carbon monoxide and hydrogen are consumed or absorbed accurately at a molar ratio of 1:1. Accordingly, because a component which is supplied in excess remains unreacted, the reaction can be proceeded again if the other component is supplied at the time when the lowering of pressure is not observed. Even though it will depend upon the size of reaction vessel and the mode of reaction, it is generally most effective to feed carbon monoxide and hydrogen in a molar ratio of 1:1.

In any case, the supply of pure carbon monoxide is satisfactory, however, the coexistence of gases which are inert to the carbonylation can be allowed.

When the reaction is carried out in the coexistence of water, the aimed α-(3-benzoylphenyl)propionic acid is produced directly. In this case, the use of water-miscible solvents such as acetone, tetrahydrofuran, dioxane which do not restrain the carbonylation, is sometimes preferable.

Meanwhile, when the reaction is carried out in the coexistence of a lower alcohol having 1 to 4 carbon atoms, the alkyl ester of α-(3-benzoylphenyl)propionic acid is produced, which alkyl ester is easily converted into α-(3-benzoylphenyl)propionic acid by conventional hydrolysis. More particularly, the alkyl ester is heated together with an aqueous solution of caustic soda, then acidified with hydrochloric acid or sulfuric acid and the free carboxylic acid is extracted with an organic solvent.

Furthermore, α-(3-benzoylphenyl)propionaldehyde of the reaction product with hydrogen is converted into the aimed product of α-(3-benzoylphenyl)propionic acid by oxidizing the former by conventionally known oxidation such as permanganate oxidation, hypochlorite oxidation, oxygen oxidation or silver oxide oxidation, which is followed by an easy separation process of extraction with an aqueous solution of an alkali such as caustic soda.

The carbonylation is carried out at a temperature in the range of 40° to 200° C., preferably 50° to 180° C. If the reaction temperature is below 40° C., the rate of reaction is very low which is not acceptable in industrial production processes. On the other hand, if the reaction temperature is above 200° C., it is not desirable because side reactions of polymerization and decomposition of transition metal carbonylation catalyst are caused to occur.

The reaction pressure at 5 kg/cm$^2$ or above can be selected arbitrarily. When the reaction pressure is lower than 5 kg/cm$^2$, the rate of reaction is very low, which cannot be adopted practically. When the reaction pressure is higher, the reaction proceeds faster, however, too high pressure necessitates a very high pressure resistance for a reaction vessel, so that there is naturally a limit in view of the designing of reaction equipment. Accordingly, the pressure lower than 500 kg/cm$^2$ is sufficient in a practical viewpoint.

In the above carbonylation, it is possible to use a solvent which is inert to the reaction in order to remove the heat of reaction or the like. Exemplified as the solvents which are inert to the carbonylation are polar solvents such as ethers, ketones and alcohols, and nonpolar solvents such as paraffins, cycloparaffins and aromatic hydrocarbons. However, satisfactory results can be obtained generally without any solvent as far as reaction materials are in a liquid state under the reaction conditions.

In the carbonylation of the step (II), 3-ethylbenzophenone of the formula (A) that is contained in the reaction mixture of the step (I) is not changed substantially, while 3-ethenylbenzophenone of the formula (B) is converted into the aimed product of α-(3-benzoylphenyl)propionic acid derivative by this carbonylation.

Furthermore, in this step (II), 3-ethylbenzophenone of the formula (A) and the aimed product of α-(3-benzoylphenyl)propionic acid which are contained in the reaction product of the carbonylation using water can be separated quite easily, for example, by the extraction with aqueous alkaline solution. The alkyl ester of α-(3-benzoylphenyl)propionic acid of the product of reaction with alcohol can be easily separated by conventional separation method such as distillation. Still further, α-(3-benzoylphenyl)propionaldehyde of the product of reaction with hydrogen can be easily separated likewise by conventional separation method such as distillation.

Therefore, according to the method of the present invention, it is possible to produce a pure aimed product. The 3-ethylbenzophenone of the formula (A) which was separated from the reaction mixture of the step (II) can be reused as the material used for the step (I).

In the following, the present invention will be described in more detail with reference to examples.

BEST METHOD FOR CARRYING OUT THE INVENTION

EXAMPLE 1

Step (I): Dehydrogenation (No. 1)

An iron oxide dehydrogenation catalyst of G-64C (trademark) made by Nissan Girdler Catalysts Co., Ltd. of 15 to 25 mesh in particle size was used.

3-Ethylbenzophenone (10 ml/hr) and 200 ml/hr of water were continuously fed to a reaction tube at 560° C. By cooling the outlet of reaction tube, the reaction product was liquefied and left to stand still to separate. The oily layer was distilled at a reduced pressure of 2 to 3 mm Hg to obtain a fraction of 90° C. to 160° C. in distilling temperature (Recovery: 85%). This product was analyzed by gas chromatography.

In this fraction, 28.3% of 3-ethenylbenzophenone and 61.0 of 3-ethylbenzophenone were contained.

EXAMPLE 2

Step (I): Dehydrogenation (No. 2)

The dehydrogenation of 3-ethylbenzophenone and the after-treatment were carried out in the like manner as in Example 1 except that a chromium oxide/iron oxide dehydrogenation catalyst of G-64A (trademark) made also by Nissan Girdler Catalysts Co., Ltd. was used and reaction was carried out at 540° C.

According to the result of analysis with regard to the fraction obtained by distillation, 15.8% of 3-ethenylbenzophenone and 78.9% of 3-ethylbenzophenone were contained.

EXAMPLE 3

Step (I): Dehydrogenation (No. 3)

The dehydrogenation of 3-ethylbenzophenone and the after-treatment were carried out in the like manner as in Example 1 except that an iron oxide dehydrogenation catalyst containing magnesia which was prepared by the following procedure was used and reaction was carried out at 570° C.

According to the result of analysis with regard to the fraction obtained by distillation, 39.4% of 3-ethenylbenzophenone and 49.1% of 3-ethylbenzophenone were contained.

Preparation of Catalyst Containing Magnesia

Ferric sulfate (550 g) was dissolved in 3 liter of water and precipitate was removed. An aqueous solution of copper sulfate of 160 g/500 ml was added thereto and it was poured into an aqueous suspension of magnesia of 958 g/8 liter. The precipitate was filtered off and washed with water, and it was suspended in 10 liter of water and 73 g/300 ml of potassium carbonate was added thereto. After drying, it was sintered at 650° C. for 3 hours and molded by adding water.

EXAMPLE 4

Step (II): Carbonylation
(Formation of Ester, No. 1)

The fraction (100 g) obtained in Example 1, 20 g of methyl alcohol, 170 mg of palladium chloride and 0.5 g of triphenylphosphine were fed into a 500 ml autoclave equipped with a stirrer. The pressure was maintained at 90 kg/cm$^2$ with carbon monoxide and reaction was carried out at 120° C. for 12 hours. After the reaction, it was cooled and unchanged gas was discharged. Then, reduced pressure distillation at 2 mm Hg to 3 mm Hg was carried out to obtain 63.0 g of a fraction (a) of 120° C. to 150° C. in distilling temperature and 34.4 g of a fraction (b) of 152° C. to 165° C. in distilling temperature.

The composition of the fraction (a) was 92.1% of 3-ethylbenzophenone. The purity of α-(3-benzoylphenyl)propionic acid methyl ester of the fraction (b) was 87.5% and the ratio of α-aryl compound/β-aryl compound was 31.2.

EXAMPLE 5

Step (II): Carbonylation
(Formation of Ester, No. 2)

The reaction product obtained in the step (I) was carbonylated in the like manner as in Example 4 except that 0.68 g of dichloropalladium bistriphenylphosphine and 0.3 g of triphenylphosphine as carbonylation catalysts were used.

The composition and recovery of a fraction (a) obtained by reduced pressure distillation were almost the same as those of Example 4. According to the results of analysis, the purity of α-(3-benzoylphenyl)propionic acid methyl ester of a fraction (b) was 87.9% and the ratio of α-aryl compound/β-aryl compound was 28.4.

EXAMPLE 6

Step (II): Carbonylation
(Formation of Ester, No. 3)

Carbonylation was carried out in the like manner as in Example 4 except that 40 g of sec-butyl alcohol was used in place of methyl alcohol.

The fraction of 150° C. to 162° C. in distilling temperature which was obtained by reduced pressure distillation of 0.5 mm Hg to 1 mm Hg was sec-butyl ester of α-(3-benzoylphenyl)propionic acid.

REFERENCE EXAMPLE 1

Preparation of Ketoprofen by Hydrolysis of Methyl Ester

The fraction (b) obtained in Example 4 was subjected to precise fractional distillation to obtain a fraction of α-(3-benzoylphenyl)propionic acid methyl ester of 137° C. to 142° C. in distilling temperature at 0.5 mm Hg to 1 mm Hg (purity: 97.8%, ratio of α-aryl compound/β-aryl compound: 71).

The above fraction (25.4 g) and 150 ml of 5% caustic soda aqueous solution were mixed together. This mixture was subjected to hydrolysis for 5 hours at refluxing temperature. After cooling, the reaction product was acidified by the addition of hydrochloric acid and precipitated solid substance was extracted with chloroform. The chloroform was then removed by evaporation to obtain a solid substance, which was recrystallized by using benzene/petroleum ether to obtain 20.7 g of α-(3-benzoylphenyl)propionic acid (trade name: Ketoprofen). The melting point and spectrum were the same as those of an authentic sample.

It was confirmed also that Ketoprofen was obtained likewise by hydrolyzing similarly the alkyl esters of Examples 5 and 6.

EXAMPLE 7

Step (II): Carbonylation
(Formation of Carboxylic acid)

The fraction (43 g) obtained in Example 1, 5.5 g of bisdichlorotriphenylphosphine palladium, 80 g of 10% aqueous solution of hydrochloric acid and 80 ml of toluene as a solvent were fed into a 500 ml autoclave equipped with a stirrer. The pressure was raised to 100 kg/cm$^2$ with carbon monoxide at room temperature and further pressurized to 300 kg/cm$^2$ with heating to 120° C. After the absorption of carbon monoxide by reaction was ceased, the reaction was continued for 24 hours.

After the reaction, the autoclave was cooled and recovered the reaction mixture, which was diluted with 400 ml of chloroform. Using a separating funnel, an oily layer and an aqueous layer were separated and the oily layer was extracted three times with each 50 ml of 8% aqueous caustic soda solution. Hydrochloric acid was then added to make the aqueous extract pH 2. After that, it was extracted with 500 ml of chloroform three times and chloroform was removed from the obtained extract by reduced pressure evaporation to obtain a solid substance. It was recrystallized by using benzene/petroleum ether to obtain 10.1 g of α-(3-benzoylphenyl)propionic acid. The melting point and absorption spectrum were the same as those of an authentic sample.

EXAMPLE 8

Step (II): Carbonylation
(Formation of Aldehyde, No. 1)

The fraction (100 g) obtained in Example 1, 100 mg of rhodium hydridotristriphenylphosphine, and 60 mg of triphenylphosphine were fed into a 500 ml autoclave equipped with a stirrer. The pressure was maintained at 90 kg/cm$^2$ with a mixed gas of carbon monoxide and hydrogen of 1:1 in molar ratio and reaction was carried out at 110° C. for 12 hours. After the reaction, it was cooled and unchanged gas was discharged. Then, reduced pressure distillation was carried out to obtain 61.2 g of a fraction (a) of 105° C. to 133° C. in distilling temperature and 33.4 g of a fraction (b) of 128° C. to 144° C. in distilling temperature at reduced pressure of 0.5 mm Hg to 1 mm Hg.

The fraction (a) was 3-ethylbenzophenone and the fraction (b) was α-(3-benzoylphenyl)propionaldehyde (purity: 86.9%) and the ratio of α-aryl compound/β-aryl compound was 15.3.

EXAMPLE 9

Step (II): Carbonylation
(Formation of Aldehyde, No. 2)

The reaction product obtained in the step (I) was carbonylated in the like manner as in Example 8 except that 85 mg of iridium hydridocarbonyltristriphenylphosphine and 60 mg of triphenylphosphine as carbonylation catalysts were used.

The composition and recovery of a fraction (a) obtained by reduced pressure distillation were almost the same as those of Example 8. The fraction (b) was α-(3-benzoylphenyl)propionaldehyde (purity: 86.1%) and the ratio of α-aryl compound/β-aryl compound was 12.1.

REFERENCE EXAMPLE 2

The fraction (b) obtained in Example 8 was subjected to precise fractional distillation to obtain a fraction of α-(3-benzoylphenyl)propionaldehyde of 134° C. to 139° C. in distilling temperature at reduced pressure of 0.5 mm Hg to 1 mm Hg (purity: 97.6%). The ratio of α-aryl compound/β-aryl compound was 49.8.

The obtained propionaldehyde (15 g), 0.03 g of cobalt naphthenate and 180 ml of decane as a solvent were fed into a 300 ml autoclave and reaction was carried out for 16 hours at 70° C. with maintaining a pressure of 10 kg/cm$^2$ by oxygen.

After the reaction, decane was removed to obtain a solid substance and it was washed with 500 ml of water and dissolved in 500 ml of chloroform, and washing with water was repeated further three times and the chloroform was removed under reduced pressure. The thus obtained solid substance was recrystallized with benzene/petroleum ether to obtain 10 g of α-(3-benzoylphenyl)propionic acid (trade name: Ketoprofen). The melting point and absorption spectrum of the compound were the same of those of an authentic sample.

Meanwhile, oxidation using permanganate was also carried out. That is, 36 g of the above propionaldehyde fraction was dissolved in 250 ml of benzene and 250 ml of water was further added, which was followed by vigorous stirring to suspend. With maintaining the suspended state, 1 liter of 2% potassium permanganate aqueous solution was added slowly dropwise over 2 hours. The reaction was carried out for 18 hours at room temperature with continuing the stirring after the dropping.

After the reaction, the reaction mixture was acidified by the addition of concentrated sulfuric acid and 18 g of sodium sulfite was added. 500 ml of water was further added and it was extracted with 150 ml of chloroform three times. The chloroform solution was washed with water and it was then extracted with 5% caustic soda aqueous solution.

The obtained aqueous layer was acidified by the addition of hydrochloric acid and the solid substance which was separated out was extracted with chloroform. The chloroform was removed by evaporation to obtain a solid substance, which was recrystallized with benzene/petroleum ether to obtain 23 g of α-(3-benzoylphenyl)propionic acid (trade name: Ketoprofen). The melting point and absorption spectrum were the same as those of an authentic sample.

It was confirmed that Ketoprofen can be also obtained by oxidizing likewise the propionaldehyde in Example 9.

INDUSTRIAL APPLICABILITY

According to the method of the present invention, highly pure α-(3-benzoylphenyl)propionic acid derivatives, which are medicines per se or which can easily afford the same, can be produced efficiently and economically in a simple process from a readily available basic chemical product of 3-ethylbenzophenone.

We claim:

1. A method of producing α-(3-benzoylphenyl)propionic acid derivatives which is characterized in the following step (I) and step (II), step (I):
   a step of vapor phase dehydrogenation by bringing 3-ethylbenzophenone represented by a formula (A) into contact with a dehydrogenation catalyst in the coexistence of an inert gas through a fixed bed flow method to obtain 3-ethenylbenzophenone represented by a formula (B), and step (II):
   a step to obtain α-(3-benzoylphenyl)propionic acid derivative represented by a general formula (C) in which 3-ethenylbenzophenone represented by the formula (B) obtained in the step (I) is subjected to carbonylation with carbon monoxide and hydrogen or with carbon monoxide and water or a lower alcohol having 1 to 4 carbon atoms at a temperature of 40° C. to 200° C. and a reaction pressure of 5 kg/cm$^2$ or above in the presence of a transition metal complex carbonylation catalyst,

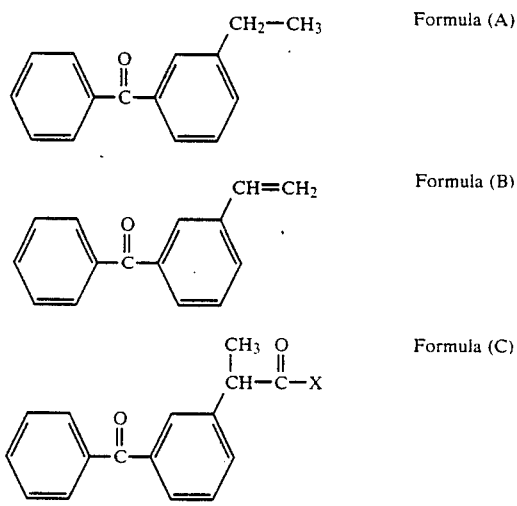

wherein X is hydrogen, a hydroxyl group or an alkoxyl group having 1 to 4 carbon atoms.

2. The method as claimed in claim 1, wherein said dehydrogenation catalyst is iron oxide catalyst and/or chromium oxide catalyst.

3. The method as claimed in claim 1, wherein the metal of said transition metal complex carbonylation catalyst is a transition metal selected from Pd, Pt, Rh, Ir and Ru.

4. The method as claimed in claim 1, wherein the temperature of said dehydrogenation reaction is 400° to 650° C., and the pressure is from reduced pressure to 10 kg/cm$^2$.